US010052502B1

(12) United States Patent
Mayer

(10) Patent No.: US 10,052,502 B1
(45) Date of Patent: Aug. 21, 2018

(54) LET AREAL DETECTOR FOR PROTONS USING RADIOCHROMIC FILM

(71) Applicant: Rulon Mayer, Garrett Park, MD (US)

(72) Inventor: Rulon Mayer, Garrett Park, MD (US)

(73) Assignee: Rulon Mayer, Garrett Park, MD (US)

( * ) Notice: Subject to any disclaimer, the term of this patent is extended or adjusted under 35 U.S.C. 154(b) by 0 days.

(21) Appl. No.: 15/485,932

(22) Filed: Apr. 12, 2017

(51) Int. Cl.
*A61N 5/10* (2006.01)
*G01T 1/06* (2006.01)

(52) U.S. Cl.
CPC ......... *A61N 5/1071* (2013.01); *A61N 5/1031* (2013.01); *G01T 1/06* (2013.01); *A61N 2005/1087* (2013.01)

(58) Field of Classification Search
CPC ....... A61N 5/1071; A61N 5/1031; G01T 1/06
See application file for complete search history.

(56) References Cited

U.S. PATENT DOCUMENTS

| 3,226,545 A  * | 12/1965 | Potsaid ..................... G01T 1/04 250/473.1 |
| 5,164,993 A  * | 11/1992 | Capozzi .................. G06T 5/008 378/901 |
| 2015/0050349 A1* | 2/2015 | Schulte ................ A61N 5/1042 424/490 |
| 2017/0036038 A1* | 2/2017 | Scholz ................. A61N 5/1031 |

* cited by examiner

*Primary Examiner* — Hugh H Maupin

(57) ABSTRACT

The use of radiochromic film for measuring the spatial distribution of the Linear Energy Transfer (LET) deposited by protons is described. The film is dosed with a proton beam and scanned to record grey-levels of the film. The grey-levels are converted to a measured dose using calibration films and the measured dose is compared to a calculated dose to generate a scaled-normalized difference (SND) between the calculated dose and the measured dose. An improved method and apparatus for treating an abnormal condition using radiation therapy in a patient in need thereof based on a measured LET is also provided.

20 Claims, 16 Drawing Sheets

 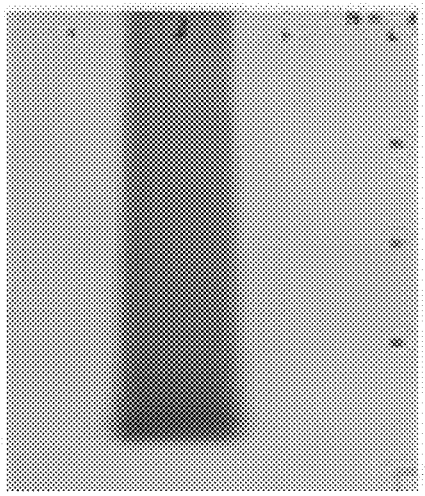 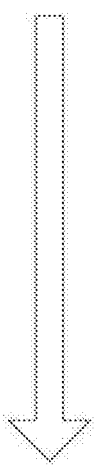 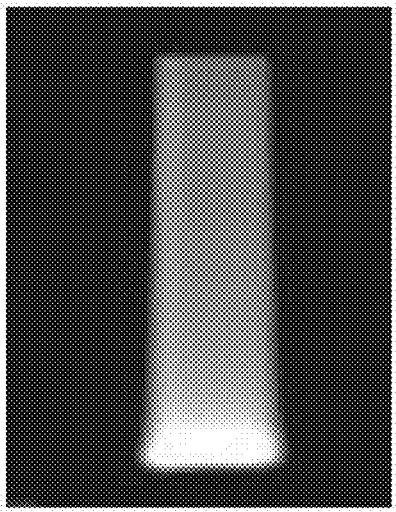
FIG. 3A                FIG. 3B
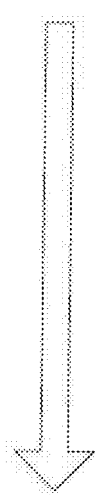 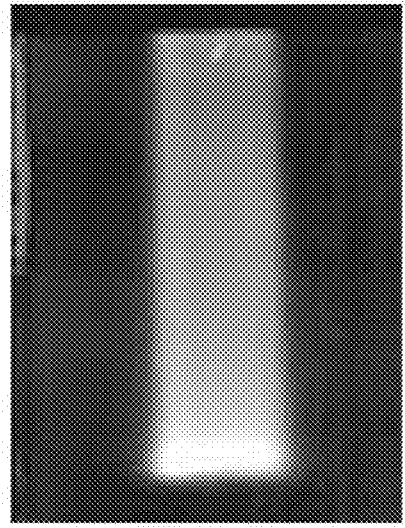 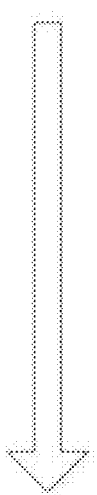 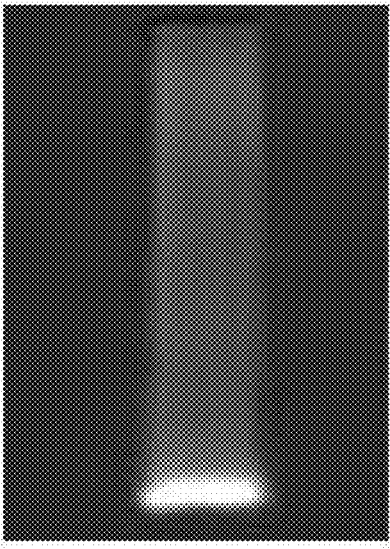
FIG. 3C                FIG. 3D

LET AREAL DETECTOR FOR PROTONS USING RADIOCHROMIC FILM

STATEMENT REGARDING FEDERALLY SPONSORED RESEARCH OR DEVELOPMENT

Part of the work performed during development of this invention utilized U.S. Government funds through Department of Defense grant number W81XWH-0920174. The U.S. Government has certain rights in this invention.

CROSS REFERENCE

U.S. Pat. No. 5,331,164
Inventors: Buehler; Martin G. (La Canada, Calif.), Blaes; Brent R. (San Dimas, Calif.), Lieneweg; Udo (Altadena, Calif.)
Assignee: California Institute of Technology (Pasadena, Calif.)
Family ID: 24699670
Application Ser. No. 07/672,705
Filed: Mar. 19, 1991

FIELD OF THE DISCLOSURE

The present disclosure relates to preferential radiation delivery to targets, such as tumors, while minimizing dose to sensitive organs. More specifically, the present disclosure relates to direct measurement of high Linear Energy Transfer (LET) of proton beams used to treat tumors and the use of these measurements to improve treatment planning and delivery to a patient tumor.

BACKGROUND

In the discussion that follows, reference is made to certain structures and/or methods. However, the following references should not be construed as an admission that these structures and/or methods constitute prior art. Applicants expressly reserve the right to demonstrate that such structures and/or methods do not qualify as prior art against the present invention.

Radiation therapy depends on predictably and reliably delivering dose to tumors and sparing normal tissues. High energy protons that are currently being used to treat tumors exploit the proton's relative advantageous dose deposition characteristics. Protons with kinetic energy of a few hundred MeV can selectively deposit dose to deep seated tumors without an exit dose as a difference to x-rays. High energy x-rays dose deposition diminishes the further the x-rays penetrate the material. To achieve higher dose to the tumor, multiple photon beams are used. Protons, in contrast, the maximum dose inside the material can reach a maximum for a single beam (i.e., "Bragg peak") and is controllable by changing the proton energy, something that is impossible to achieve with xrays. In other words one can deliver higher dose to tumors but with lower does to sensitive normal tissues. This can result in better cures with lower toxicity to normal tissues.

Due to the Bragg peak, high energy (mega electron volts) protons more selectively deliver maximal doses into desired areas with reduced radiation at the distal and proximal regions relative to photons. The Bragg peak can be sharp (<1 cm). The proton beams may be broadened using energy modulation to cover larger tumors both distally and proximally. The modulated proton beam is known as a Spread Out Bragg Peak (SOPB). The high dose regions are attributed to protons slowing down near the end of the range. These slowing protons deliver doses within a short distance and can yield a high Linear Energy Transfer (LET). The high rate of energy deposition within short distances has been correlated with high biological lethality. Previously, the LET was only measured at a given fixed point and the LET spatial distribution was inferred from calculations.

Treatment planning controls how patients are treated. Currently treatment planning systems do not use LET information, just dose. The treatment planning systems only compute the physical dose and the biological effect is inferred from clinical experience. But for high LET particles (e.g., distal edge of proton Bragg peak, ion beams), the biological response is quite dependent on the LET. Previously, there was no measurement of LET over an area so conventionally therapy avoids this entire issue and is forced to be performed conservatively because it is unexplored and unknown.

SUMMARY

Generally, effective treatment of tumors depends on preferential radiation delivery to the targets and minimizing dose to sensitive organs. Applicants have investigated a possible method to measure the LET deposited by a proton beam over extended areas using a film dosimeter (e.g., radiochromic Gafchromic EBT2 film). This new tool can potentially measure and test LET in clinically significant configurations such as regions involving tissue heterogeneity. The radiochromic film, unlike the BANG gel may possibly be applied for measuring the LET in variable density regions by inserting the film between suitable phantom materials. This modified film methodology provides an experimental areal LET measurement that can verify Monte Carlo measurements and support inferences from current LET point measurements. These LET measurements may enhance biologically-based treatment planning for protons. More precise measurements may also help refine and determine the polymerization model and process.

Traditionally radiochromic films are used to measure dose distribution but not for LET distribution. By contrast, the claimed invention uses these films for measuring the spatial distribution of the LET deposited by protons. The radiochromic film sensitivity diminishes for large LET, but a mathematical model correlating the film sensitivity and LET is presented herein to justify relating LET and radiochromic film sensitivity (RS). Protons were directed parallel to radiochromic film sandwiched between solid water slabs. The metric describing the LET is the scaled-normalized difference (SND) between the Treatment Planning System (TPS) and measured dose. The SND is correlated with a Monte Carlo (MC) calculation of the LET spatial distribution for a large range of SNDs. A polynomial fit between the SND and MC LET is generated for protons having a single range of 20 cm with narrow Bragg peak. Coefficients from these fitted polynomial fits were applied to measured proton dose distributions with a variety of ranges. An identical procedure was applied to the protons deposited from Spread Out Bragg Peak (SOPB) and modulated by 5 cm. Gamma analysis is a method for comparing the calculated LET with the LET measured using radiochromic film at the pixel level over extended areas. Failure rates using Gamma analysis are calculated for areas in the dose distribution using parameters of 25% of MC LET, and 3 mm. The processed dose distributions finds 5 to 10% failure rates for the narrow 12.5 and 15 cm proton ranges and 10 to 15% for proton ranges of 15, 17.5 and 20 cm and modulated by 5 cm.

It is found through Gamma analysis that the measured proton energy deposition in radiochromic film and TPS can be used to determine LET. This modified film dosimetry provides an experimental areal LET measurement that can verify MC calculations, support LET point measurements, possibly enhance biologically-based proton treatment planning, and determine the polymerization process within the radiochromic film.

Treatment planning systems in accordance with the claimed invention can more directly compute the biological effect (i.e., probability of controlling a tumor normal tissue complications) that includes how energy is deposited. For example, if LET is incorporated into the planning, multiple beam matching may occur by matching the distal edges of the Bragg peak instead of using dose matching. Traditionally, tumors are considered to be a single tissue but they are in fact heterogeneous and high LET particles should help control them as well.

An exemplary method of treating an abnormal condition using radiation therapy in a patient in need thereof, includes: subjecting the patient to a radiation source for at least one time point and measuring the Linear Energy Transfer (LET) deposited by a proton beam over one or more extended areas by analyzing a film dosimeter, determining a focused target area for the radiation treatment of the patient using the measured LET over at least one of the one or more extended areas, and dosing the focused target area of the patient with a therapeutically effective amount of radiation.

An exemplary apparatus for treating a patient includes: a proton beam generator configured to provide a proton beam to a patient and a beam shaper to shape the proton beam to a focused target area of the patient. The beam shaper is capable of being configured based on a previously measured Linear Energy Transfer (LET) deposited by a proton beam over an extended area.

An exemplary method of measuring Linear Energy Transfer (LET) deposited over an area includes: dosing a film with a proton beam, scanning the film to record grey-levels of the film, converting the grey-levels to a measured dose using calibration films, and comparing the measured dose to a calculated dose to generate scaled normalized difference (SND) between the calculated dose and the measured dose.

BRIEF DESCRIPTION OF THE DRAWING

The following detailed description of preferred embodiments can be read in connection with the accompanying drawings in which like numerals designate like elements and in which:

FIGS. 3A-D are exemplary images of exposed radiochromic film. FIG. 3A is an image of a proton exposed, radiochromic film, 20 cm range. FIG. 3B is an image of TPS dose. FIG. 3C is an image of multichannel optimized dose from radiochromic film. FIG. 3D is an image of scaled normal difference (p=0) of radiochromic film.

FIG. 7A is a graph for proton range of 20 cm. FIG. 7B is a graph of profiles and corrections for proton range of 12.5 cm using parameters from proton range of 20 cm (FIG. 7A). FIG. 7O is a graph of profiles and corrections for proton range of 15 cm using parameters from proton range of 20 cm (FIG. 7A).

DETAILED DESCRIPTION

Figure 1:
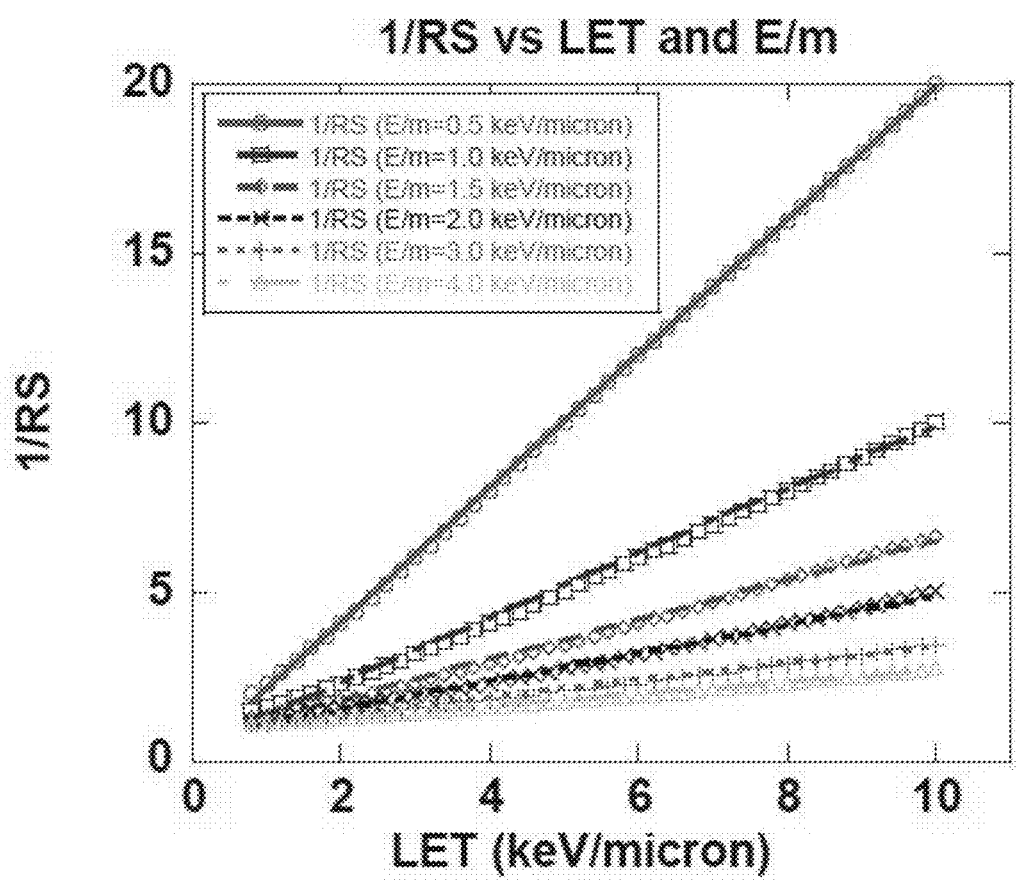
FIG. 1 is a graph of 1/RS versus LET and E/m and linear fit to Equation 4 calculation.

Effective treatment of tumors depends on preferential radiation delivery to the targets and minimizing dose to sensitive organs. Due to the Bragg peak, high energy (mega electron volts) protons more selectively deliver maximal doses into desired areas with reduced radiation at the distal and proximal regions relative to photons. The Bragg peak can be sharp (<1 cm). The proton beams may be broadened using energy modulation to cover larger tumors both distally and proximally. The modulated proton beam is known as a Spread Out Bragg Peak (SOPB). The high dose regions are attributed to protons slowing down near the end of the range. These slowing protons deliver doses within a short distance and can yield a high Linear Energy Transfer (LET). The high rate of energy deposition within short distances has been correlated with high biological lethality. Until recently, direct measurement of LET is accomplished by using point dosimeters through specially designed and configured ionization chambers. Specifically, current techniques measure LET use tissue-equivalent proportional counters, solid-state spectrometers, and other methods. Preliminary proof of principle studies used a BANG gel to explore the possibility of measuring LET over extended volumes. The claimed invention includes a method to measure the LET deposited by a proton beam over extended areas using a film dosimeter (radiochromic Gafchromic EBT2 film). Radiochromic film is equally sensitive to most kinds of radiation, but the film sensitivity is diminished in the distal regions of the Bragg peak.

For example, radiochromic film EBT2 is a two-dimensional detector composed of a single sensitive polymer layer (28 microns) sandwiched between protective sheets. The material composition is close to being tissue equivalent. Ionizing radiation initiates polymerization within the sensitive layer and promotes film darkening. The film is scanned, digitized and the darkening correlated with dose. High LET radiation with limited range leads to under detected dose. There are at least two possible mechanisms for reduced sensitivity. First, both x-ray film and radiochromic film may suffer from localized saturation for high LET particles and high density of particle tracks or quenching. For x-ray film, unlike radiochromic film, the detection sensitivity depends on radiation energy and has significant non-linear optical density and dose relationship. Alternatively, one can examine the quenching problem by generating Monte Carlo simulations for radiochromic films containing two sensitive layers rather than one. With respect to radiochromic film quality factors, one study found that the relative proton stopping powers for protons exceeding 1 MeV was constant but varied substantially for lower energies, especially for protons nearing the end of their range. Unlike x-ray film, radiochromic film quenching was purportedly due to proton loss occurring outside the sensitive layers. Radiochromic film suffers from the "quenching" effect for high LET radiation and has been observed a number of times but has rarely been analyzed or discussed in detail. More importantly, it has only been treated as a nuisance, rather than exploited for use as an areal detector for LET.

To quantitatively account for the diminished radiochromic film Relative Sensitivity (RS) and provide heuristic support for associating RS with LET, RS is related to the average number of ionizations <n> and number of polymerizations ■ for and radiochromic film, respectively. In contrast, ionization chamber detectors depend on the average number of ionizations but the radiochromic film tends to saturate for high LET radiation.

The probability of a film with monomer receiving n ionizing events from a proton can be quantified according to the Poisson probability $$P(n, \lambda) = \frac{\lambda^n}{n!} e^{-\lambda} \quad (1)$$

where □ is the Poisson parameter.

An ionization detector sensitivity $S_{Ion}$ to radiation is hypothesized to equal the average number of ionizations <n> (using Equation 1), or $$S_{Ion} = \langle n \rangle = \sum_{n=0}^{\infty} n P(n, \lambda) = \lambda \quad (2)$$

Due to quenching, radiochromic film will only generate single polymers despite receiving multiple ionizations within a monomer. In other words, if we define the polymerization per ionization factor $q_n$, $q_o$ is 0 for no ionization of the monomer and $q_n$ is 1 for all other n ionizations. The radiochromic film radiation sensitivity $S_{RC}$ (following Equation 1) is given by the polymer fraction ρ i.e.

$$S_{RC} = \rho = \sum_{n=0}^{\infty} q_n * P(n, \lambda) = 0 + \sum_{n=1}^{\infty} P(n, \lambda) \quad (3)$$
$$= \left( \sum_{n=0}^{\infty} P(n, \lambda) \right) - P(0, \lambda) = 1 - e^{-\lambda}$$

saturates for high □□. Thus the relative sensitivity RS comparing radiochromic film and ionization chambers sensitivities (using equations 2, 3) is $$RS = \frac{S_{RC}}{S_{Ion}} = \frac{\rho}{\langle n \rangle} = \frac{1 - e^{-\lambda}}{\lambda} \quad (4)$$

Treatment Planning Systems (TPS) such as the Varian ECLIPSE use proton beam data collected by an ionization chamber. The TPS accurately computes the expected dose (not LET) for the desired configuration, beam energy, beam modulation etc. and is intended to be delivered to a patient. From Equation 4, the ionization chamber and radiochromic film have similar sensitivity for low ionizing LET protons (□«1). Radiochromic film sensitivity diminishes relative to ionization chambers for high ionizing LET (□»1).

$$RS \approx 1 \quad \lambda \ll 1 \quad (5)$$
$$\approx \frac{1}{\lambda} \quad \lambda \gg 1$$

The average number of ionizations within a monomer should depend on the ionizing density of the incoming proton (LET) and the proton energy E needed to liberate an electron within the monomer of size m. □, the average rate of ionization, is given by $$\lambda = \frac{LET}{E/m} \quad (6)$$

Identical results are derived in the Discussion (Equation 13) using a modified Law of Mass Action.

One aspect of the claimed invention is connecting the radiochromic film sensitivity to the proton LET. The novel Equations 4, 5 support correlating the film sensitivity and LET. Inverting Equation 4 to compute the LET is difficult. However, due to the limited extent of proton LET values (1 to 10 key/micron) and the radiochromic film properties as summarized in E/m, there is a simple relationship between LET and RS. The adiabatic ionization energy needed to release an electron for the diacetylene monomer (E=1.17 eV) with a size (m=5 Å) corresponding to an estimated E/m=2 kev/micron. FIG. 1 plots $RS_{-1}$ against LET by using Equation 4 and four E/m (0.5 to 4 kev/micron) values. In addition, a linear fit between the $RS_{-1}$ and LET is shown in FIG. 1. All four plots have correlation coefficients >0.998 between the linear fit and the calculated $RS_{-1}$. Thus $RS_{-1}$ and LET are correlated in this limited but experimentally significant range of LET values. RS is inversely related to the LET for high LET and for protons slowing down, especially at the distal end of the Bragg peak.

There are a number of relationships between the RS and proton dose. After trial and error, the following approach achieved the highest correlation between RS and LET. LET is related to the difference (r) of the calculated Treatment Planning Dose ($D_{TPS}$) and the dose measured from the radiochromic media ($D_{RC}$) via Equation 6 as follows:

$$r = \frac{D_{TPS}^{p}(D_{TPS} - D_{RC})}{D_{TPS,0}^{p+1}} \propto \frac{1}{RS} \approx \frac{LET}{\frac{E}{m}} (\lambda \gg 1) \quad (7)$$

where $D_{TPS,0}$, is a normalizer, such as the prescribed planning dose (e.g., ~200 cGy) or maximum planned dose. The experimental difference in the treatment planning dose and the measured dose ($D_{TPS}$-$D_{RC}$) is due to protons with elevated LET at the distal edge of the beam. p is a parameter in this model that offers some flexibility into the analysis required due to uncertainty of r (Equation 7).

Figures 5A, 5B:
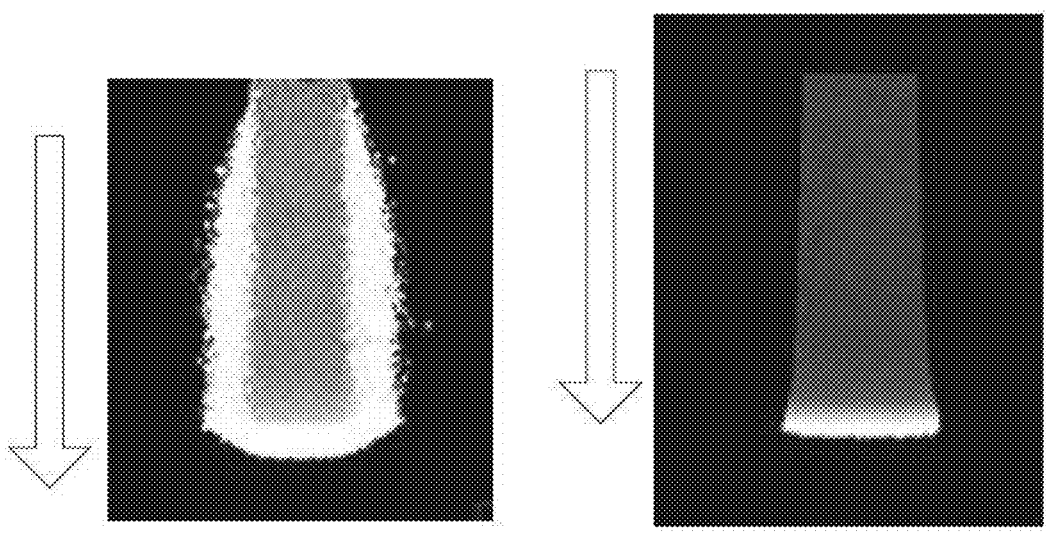
FIG. 5A is an image of LET distribution generated by Monte Carlo calculation for protons having 20 cm range.
FIG. 5B is an image of a masked LET to only include areas that get >70cGy.

The high proton LET is attributed to protons slowing at the end of their range and depositing their energy within small distances. The difference in measured and calculated doses will mostly vary with penetration depth inside the material (y) but is fa less dependent on the transverse direction (x). The largest LET variation occurs along the beam path direction where the protons are experiencing higher reductions to the primary proton energy. Secondary interactions and smaller energy degradations occur in the transverse direction. This assumption is supported by Monte Carlo calculations (FIG. 5b). One method to compute LET based on the Scaled, Normalized Difference (SND) metric presented in Equation 8.

$$LET \propto SND = \frac{D_{TPS}^{p+1}(D_{TPS} - D_{RC})}{D_{TPS,0}^{p+2}} \quad (8)$$

The SND is computed (p=0 or 1) using the registered treatment planning and measured doses at every pixel. It is empirically found that p ranges from 0 to 1. For simplicity and due to lack of precision in this methodology, the Applicants focus on only two values for p. Following this approach, the quantity SND (Equation 8) is studied to see if it can be correlated with LET in proton beams over a large dynamic range of SND values. If disparity in measured and calculated doses for protons is due to elevated LET, then the largest range R profiles (R=20 cm) can presumably be used and tested to see if it can predict disparities generated with shorter range protons and for shallower depths.

Figure 2:
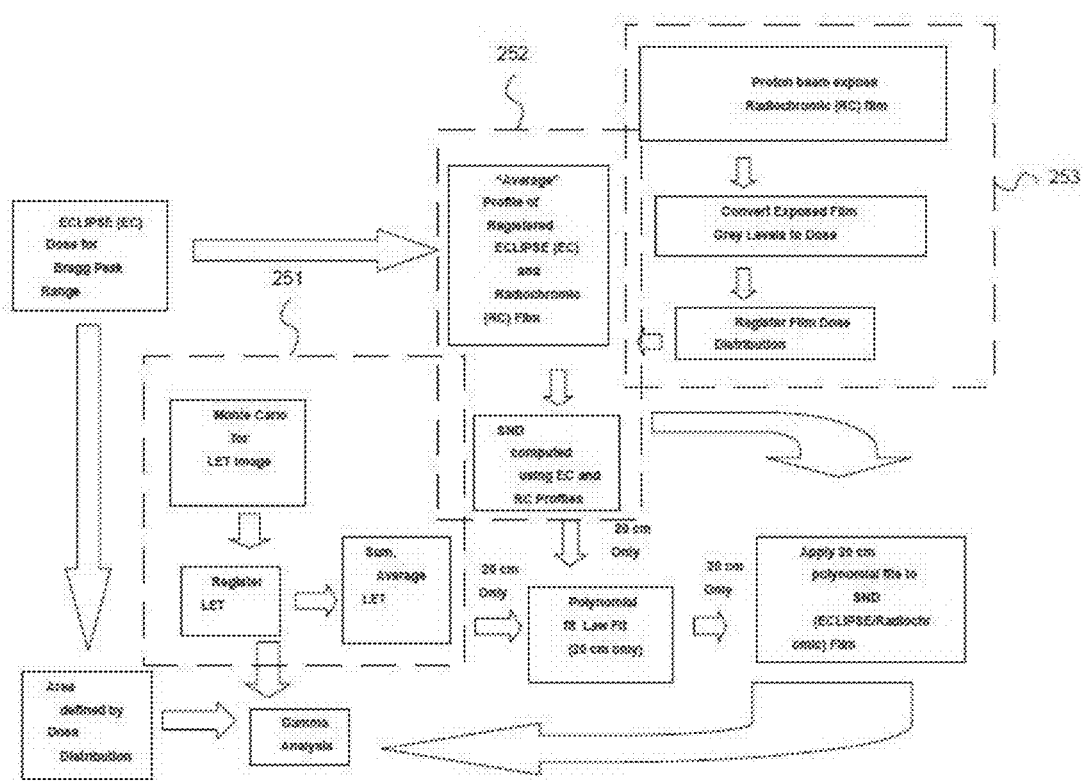
FIG. 2 is a schematic showing the processes used to generate SND from registered TPS dose, measured radiochromic film, corrections to film and comparison to MC LET.

Methods (Overview):

FIG. 2 summarizes the workflow. These ideas were tested using a pencil beam dedicated nozzle located in the Roberts Proton Therapy Center. A proton pencil beam was directed parallel to a radiochromic film sandwiched between solid water slabs. Varian ECLIPSE (EC) Treatment planning system (Blue in FIG. 2) calculated the proton dose deposition within a solid water phantom. The darkening due to the proton radiation was digitized after scanning the films with a reflective scanner (CanoScan LIDE 700F) and the film grey levels were converted to dose with the aid of calibration films. Calibration films were positioned at $D_{max}$ and exposed to 6 MeV x-rays from a Varian Trilogy machine. To autonomously handle media imperfections, a multichannel optimization approach, rather than a single red channel, was used. The multichannel approach uses all three channels (red, green, blue) to extract a single dose for each pixel. The experimentally determined dose distribution image (252 in FIG. 2) was spatially registered to the planned image using Teflon markers as fiducial indicators. These marks appeared in the CT image and as "tattoos" marked on the radiochromic film. The SND calculation used the registered images of the absolute planned dose and the detected dose and then related to the LET according to Equation 8. To validate this approach, Monte Carlo simulations (251 in FIG. 2) were generated to emulate the experimental setup. A polynomial fit ($w_{max}$ degrees) was generated for the SND and the MC LET profiles using the proton with range R=20 cm for the narrow Bragg peak and SOPB. The fit computed optimal coefficients (c(R=20 cm)$_w$) using the one dimensional profiles (Equation 9).

$$LET_{Profile}(y, R = 20 \text{ cm}) = \quad (9)$$
$$\sum_{w=0}^{w_{max}} c(R = 20 \text{ cm})_w (SND_{Profile}(y, R = 20 \text{ cm}))^w$$

These coefficients (c(R=20 cm)$_w$) were then applied to every pixel in the SND images (narrow Bragg peak, SOPB respectively) that correspond to nominal proton ranges R spanning from R=12.5 cm to 20 cm (Equation 10) to create a transformed SND image (Trans_SND). The longest range proton profile is used to extrapolate the effects of shallower penetrating particles.

$$\text{Trans\_SND}_{Image}(x, y, R) = \sum_{w=0}^{w_{max}} c(R = 20 \text{ cm})_w (SND_{Image}(x, y, R))^w \quad (10)$$

Gamma analysis was applied to the transformed SND and MC LET images. Gamma analysis is a standard technique for quantitatively comparing two sets of registered (to the pixel-level) dose or LET distributions. For Gamma Analysis, pixels within a reference LET distribution (calculated LET distribution or Monte Carlo LET) were examined and a corresponding set of pixels in the test distribution (measured film LET distribution) were searched to see if there is a matching LET. The permitted search distance criteria in two spatial directions and the permitted LET are treated as parameters and selected by the experimenter. Gamma analysis used acceptance parameters (25% of the MC LET, 3 mm. for two spatial dimensions). These acceptance criteria correspond to the minor axis for an ellipsoidal decision surface. If the reference and test LET distributions result in the metric falling outside the elliptical decision surface, then the metric is labeled a "failure", "discrepancy", or "exceedance" or there is a significant and unacceptable difference in reference and test distributions.

The proton plan (FIG. 3) was remotely generated from Walter Reed National Military Medical Center (WRNMMC) using the Varian ECLIPSE treatment planning system located at the University of Pennsylvania. CTs of the phantom were scanned at WRNMMC. The distribution shows the Bragg peak for beams (20 cm range, 5 cm width) fired from the top of the solid water. FIG. 3A shows radiochromic film exposed to protons and fiducial markers used for registration. FIG. 3B shows ECLIPSE dose distribution, FIG. 3C shows dose distribution from multichannel optimization applied to exposed film and registered to the ECLIPSE dose distribution. The SNDs (Equation 8) from the ECLIPSE treatment plan and measured radiochromic film doses were computed and shown in FIG. 3D. Only p=0 is shown for illustrative purposes.

Figure 4:
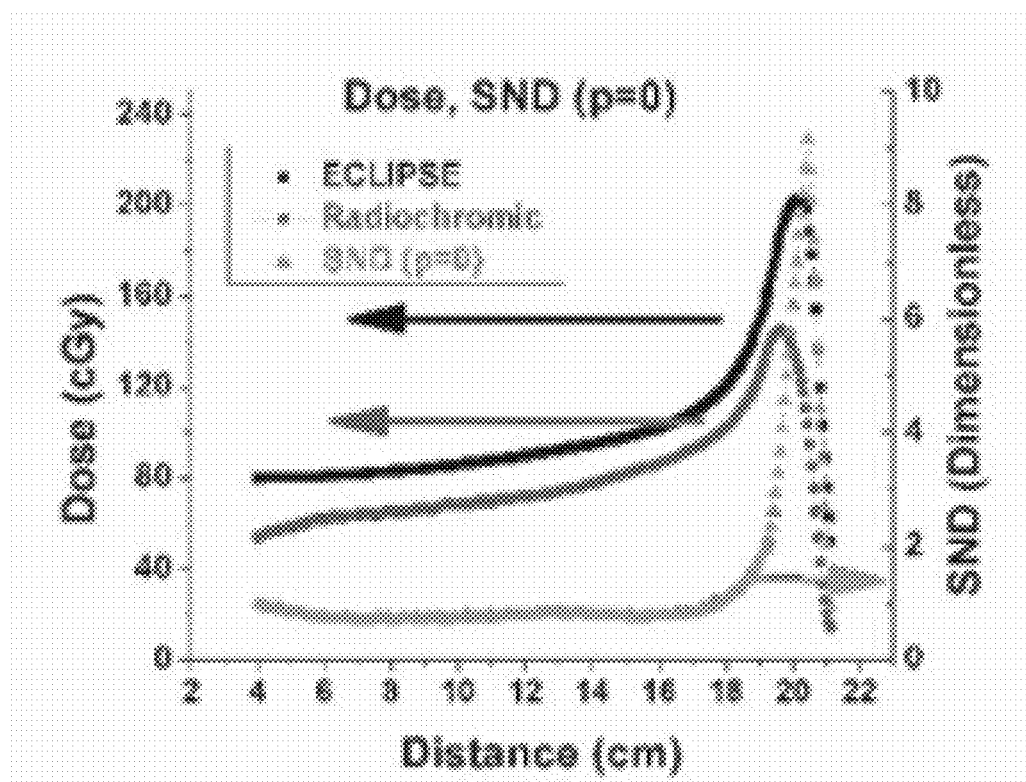
FIG. 4 is a graph of Dose Profiles for proton range of 20 cm from TPS. Multichannel optimized dose from radiochromic film, SND for p=0.

FIG. 4 plots the ECLIPSE and film dose (left axis) and SND (p=0) (right axis) against the penetration distance y. FIGS. 3 and 4 shows that deeper proton penetration (y) results in greater discrepancy between ECLIPSE dose calculation and measured film dose. The film is less sensitive to areas receiving high LET radiation relative to getting low LET. This disparity is highlighted in FIG. 4 by comparing SND (p=0, right hand axis, again for illustration) to ECLIPSE and Radiochromic film dose profiles and strongly resembles the MC LET profile (see below). Note the SND peak and LET peak is shifted distally relative to the Bragg peak.

Monte Carlo Calculation

A Monte Carlo simulation (FIG. 5A) used an in-house simulation package based on Geant4 (OpenRT) to calculate both, the dose and LET distributions of the selected beam geometries. 570,000 primary protons per spot were used at 92 different spots, which results in 52 million primaries. All particles were permitted down to zero velocity except for gammas and electrons, for which the transport threshold was set at 100 um. The simulation took 350 processor hours split on 12 processors with 2.6 GHz with 4 Gb RAM each. The dose averaged LET was calculated.

FIG. 5A shows the LET distribution for protons bombarding solid water from the top. The central region corresponds to high energy protons. Near the end of the Bragg peak, the protons slow down considerably depositing energy over short distances resulting in high LET. Outside the field, the fluence is low, but these low energy protons deposit high LET radiation. FIG. 5B shows a masked region that delineates the actual area of study and only includes areas that exceed 70 cGy. Visually, the measured SND image (FIG. 3D) qualitatively resembles the calculated LET image (FIG. 5B.). The following section (FIG. 6) shows that MC LET and SND profiles are correlated to each other over a wide range of values.

Results

Correlation Between LET and SND Metric

Figure 6:
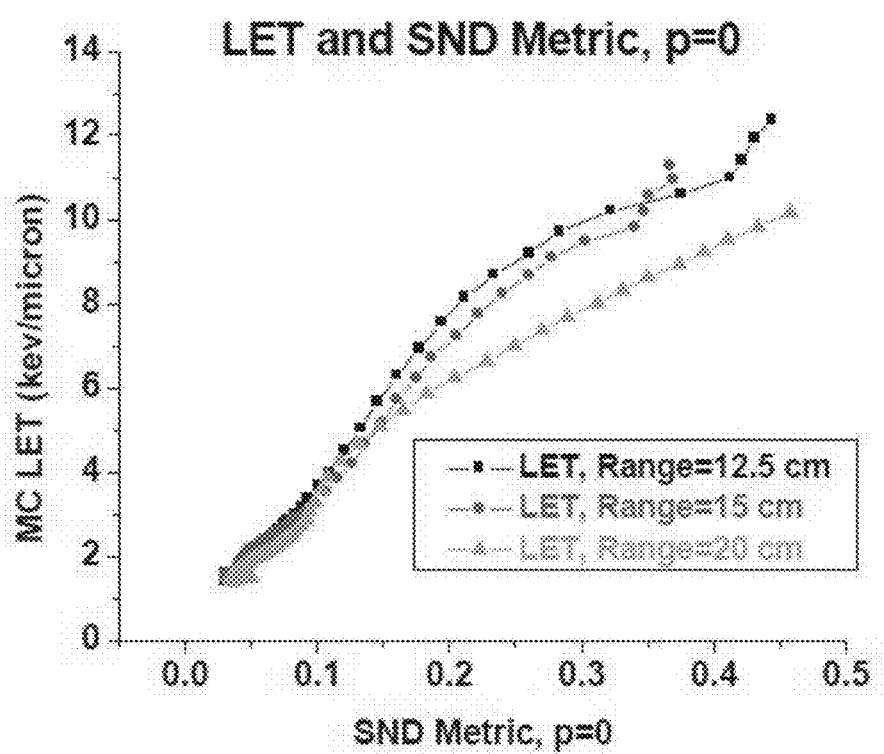
FIG. 6 is a graph of the LET and SND (p=0) relationships are shown for protons ranges, 12.5, 15, and 20 cm.

The Applicants' research assumed that the detection sensitivity only depended on LET variations and hence only on depth inside the material. One goal is finding the relationship between the SND and the LET profile generated by the Monte Carlo distribution. FIG. 6 directly shows that SND and MC LET are correlated and the curves from all proton ranges almost overlap with each other. The correlation coefficients R for the linear fit of LET to SND were 0.986, 0991, and 0.996.

The polynomial expressions (Equation 9, 10) correlating SND and LET according to FIG. 5 for the 20 cm range are used to transform the SND images into LET images (for other ranges) which are then compared with the LET distributions range (Equation 9). The coefficients from the fits are then applied to the processed (SND) radiochromic film image (Equation 10).

The gamma elliptical decision surface parameters are 3 mm in horizontal and vertical directions and 25% of Monte Carlo LET. Exceedances or failure rates were computed for areas (801 in FIG. 8A) corresponding to doses between 70 cGy and 200 cGy from the ECLIPSE dose calculation. The failure rates as measured by gamma analysis between the corrected radiochromic film and Monte Carlo LET were 6.65% for protons having a range of 20 cm with a sharp Bragg peak (FIG. 8). This illustrative example used the SND having p=0. Polynomial fit (Equation 9, 10) used $w_{max}$=5 degrees of freedom. The most significant and largest differences in LET distribution generated by the Monte Carlo calculation relative to the corrected radiochromic film appear at the entrance channel and beam edges suggesting some possible unresolved registration issues.

Figure 8A:
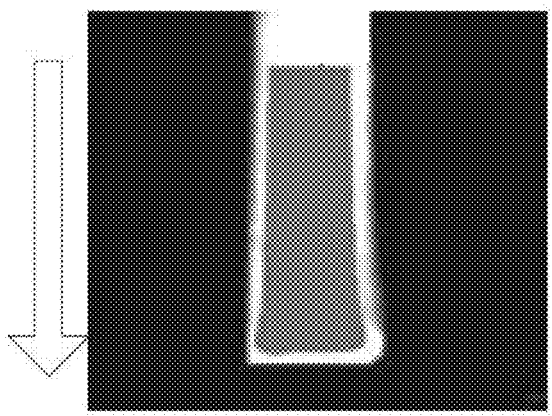
FIG. 8A is an image of a dose distribution for protons of range of 20 cm and area for gamma analysis (dose>70 cGy).
Figure 8B:
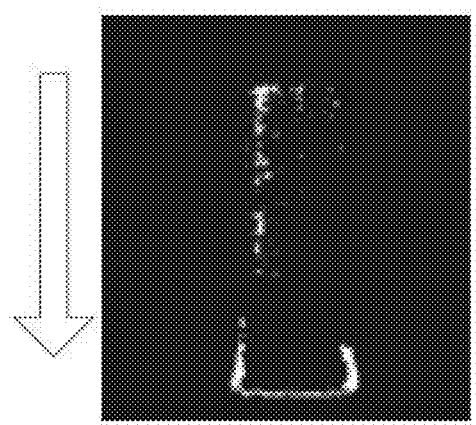
FIG. 8B is an image of gamma exceedances for MC LET and correction to SND (p=0) using 5 degrees polynomial fit.
Figure 8C:
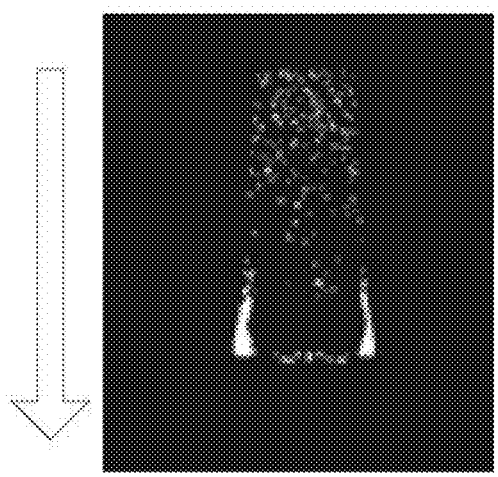
FIG. 8O is an image of gamma exceedances for MC LET and correction to SND (p=0) using 5 degrees polynomial fit for proton range 12.5 cm.
FIG. 8D is an image of gamma exceedances for MC LET and correction to SND (p=0) using 5 degrees polynomial fit for proton range 15 cm.
Figure 8D:
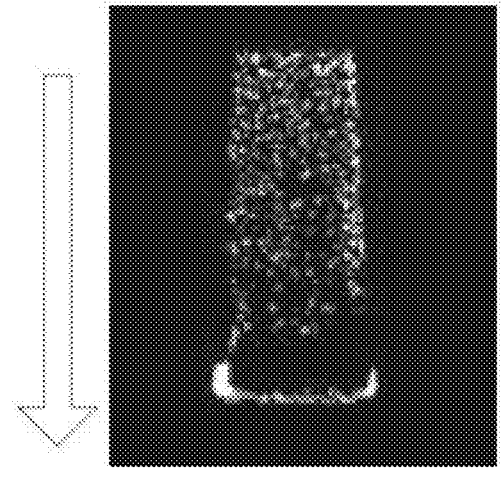

Similar displays of the gamma exceedances are shown in FIGS. 8C and 8D for protons exposing film with ranges of 12.5 and 15 cm, respectively. As in FIG. 8B, the displays used 5 degrees in the polynomial fit taken from the protons with a range of 20 cm but with the SND with p=0 for proton ranges 12.5 and 15 cm. In this case, the 9.67% and 12.2% gamma exceedances were found for areas getting dose between 70 and 200 cGy.

The exceedances shown in FIGS. 8B, 8C, and 8D mostly occur at the edges of the distal edge of the Bragg peak. In addition, there are exceedances that occur in regions with sharp dose gradients where registration is difficult but also important. The LET distribution has sharper spatial gradients than dose distributions so accurate registration is even more important.

Figure 9:
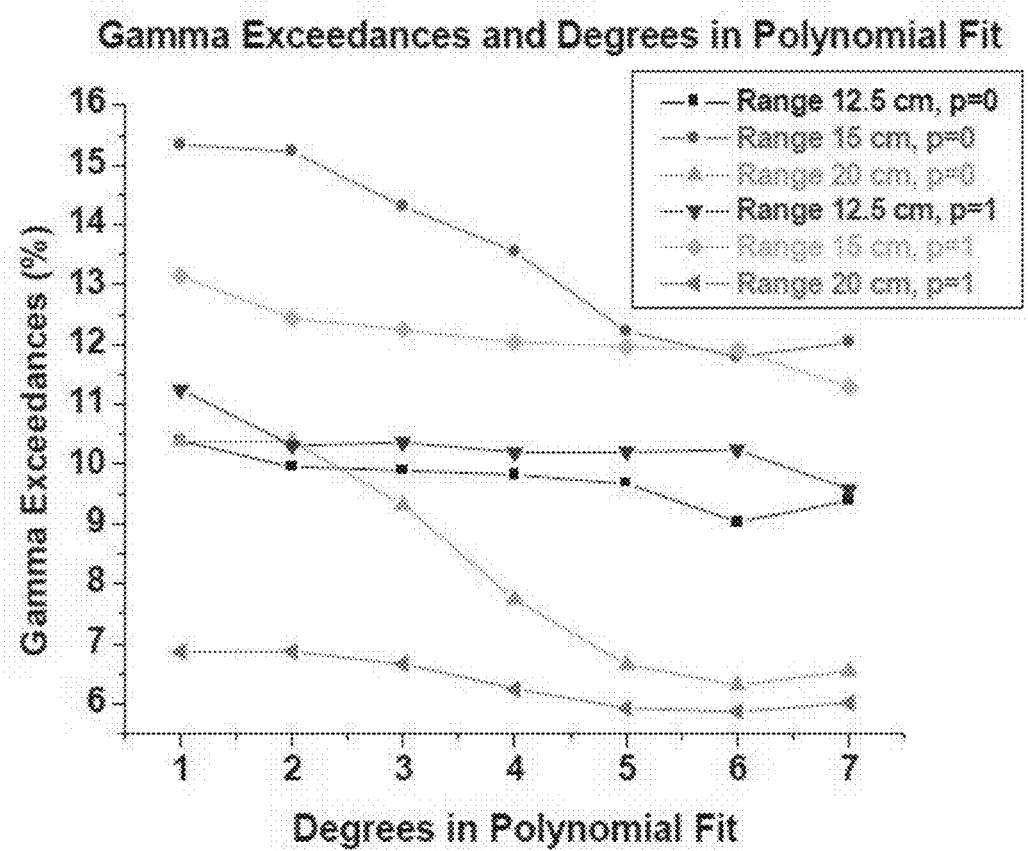
FIG. 9 is a graph of gamma exceedances for proton ranges 12.5, 15, and 20 cm using polynomial corrections with degrees varying from 1 to 7 applied to SND (p=0, 1).

The gamma exceedances as a function of number of degrees in the fit are shown in FIG. 9 for protons having ranges of 12.5, 15, and 20 cm. FIG. 9 also shows the gamma exceedances that result from using exponents of p=0 and p=1 (Equation 8). The gamma exceedances are relatively stable as a function of number of degrees in the polynomial fit, with a slight preference for higher number of degrees. The higher number of degrees however can be more unstable especially for areas with obtained from Monte Carlo.

Analysis for Pristine Bragg Peaks

Figure 7A:
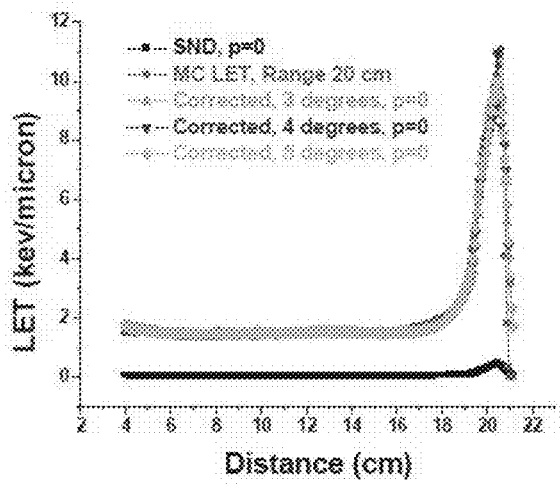
FIGS. 7A-C are graphs illustrating summed profiles along beam direction (vertical, y direction in figures). Data shows profiles for Monte Carlo LET and corrections to SND (p=0) using 3, 4, 5 degrees in polynomial fits.
Figure 7B:
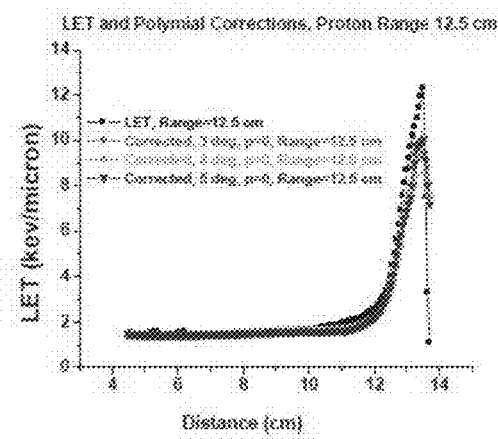
Figure 7C:
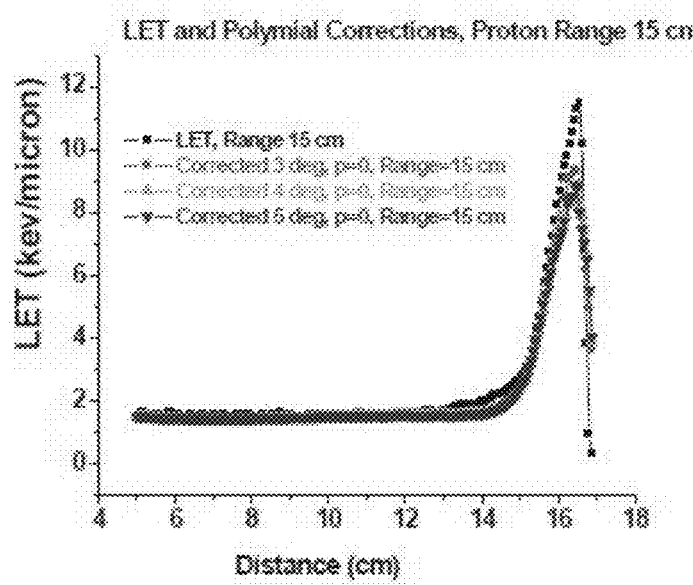

Profiles for protons with ranges of 20, 12.5, 15 cm for MC LET as well as polynomial fit using 3, 4, 5 degrees are shown in the FIGS. 7A, 7B, and 7C, respectively. The polynomial fits (with varying degrees) were generated from the averaged (in the horizontal direction) SND and LET profiles for protons having 20 cm high spatial gradients. The p=1 exponent yields slightly better and reduced number of gamma exceedances. The statistical error in the number of exceedances is small due to the large number of pixels in the region of interest (roughly 10,000). The error in the measured exceedances is due to sensitivity to spatial registration, especially at the beam edges and is roughly 1-2 percent.

A minimum detectable LET can be inferred from examining the polynomial fits of SND to LET. The average (over each of the seven fits) baseline value for LET (corresponding to SND=0) is 1.33+/−0.77 keV/micron (p=0), 1.15+/0.11 keV/micron (p=1) and 1.24 keV/micron +/−0.54 (p=0 and p=1). These minimum LET values exceed the LET for photons used for therapy and therefore cannot measure LET for photons used in the clinic.

Analysis for Spread-Out Bragg Peaks (SOBP)

Figures 10A, 10B, 10C:
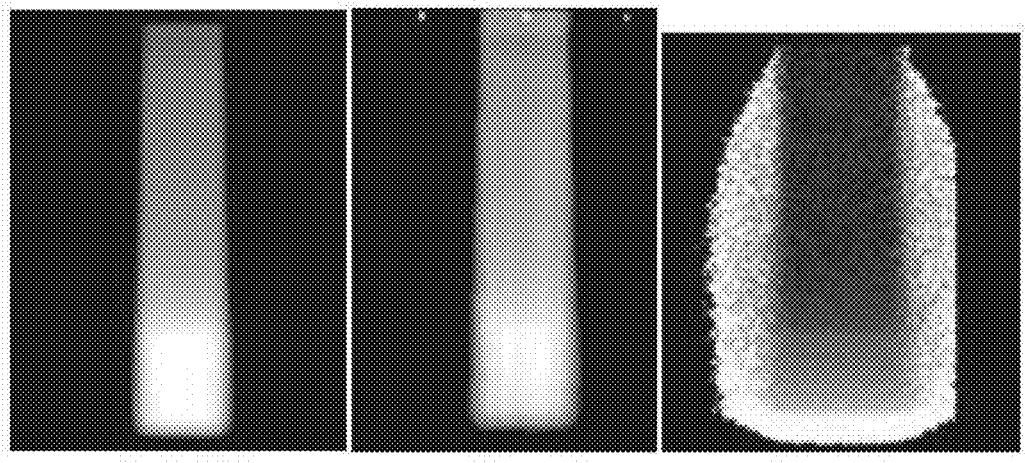
FIG. 10A is an image from an ECLIPSE plan for proton with range of 20 cm, Modulation 5 cm.
FIG. 10B is an image of a measured dose from radiochromic film plan for proton with range of 20 cm, Modulation 5 cm.
FIG. 10C is an image of a Monte Carlo calculation of LET for proton with range of 20 cm, Modulation 5 cm.

The analysis that was applied to the narrow Bragg peaks was also conducted for the SOPB with modulation of 5 cm. FIGS. 10A, 10B, and 10O show the two dimensional images of the Varian ECLIPSE calculated dose, the measured dose from the radiochromic film, and the LET Monte Carlo calculation for the SOPB for proton range of 20 cm, respectively. The broadened peak is evident in FIGS. 10A and 10B and the LET shows a more gradual increase in the broadened region.

Figure 11A:
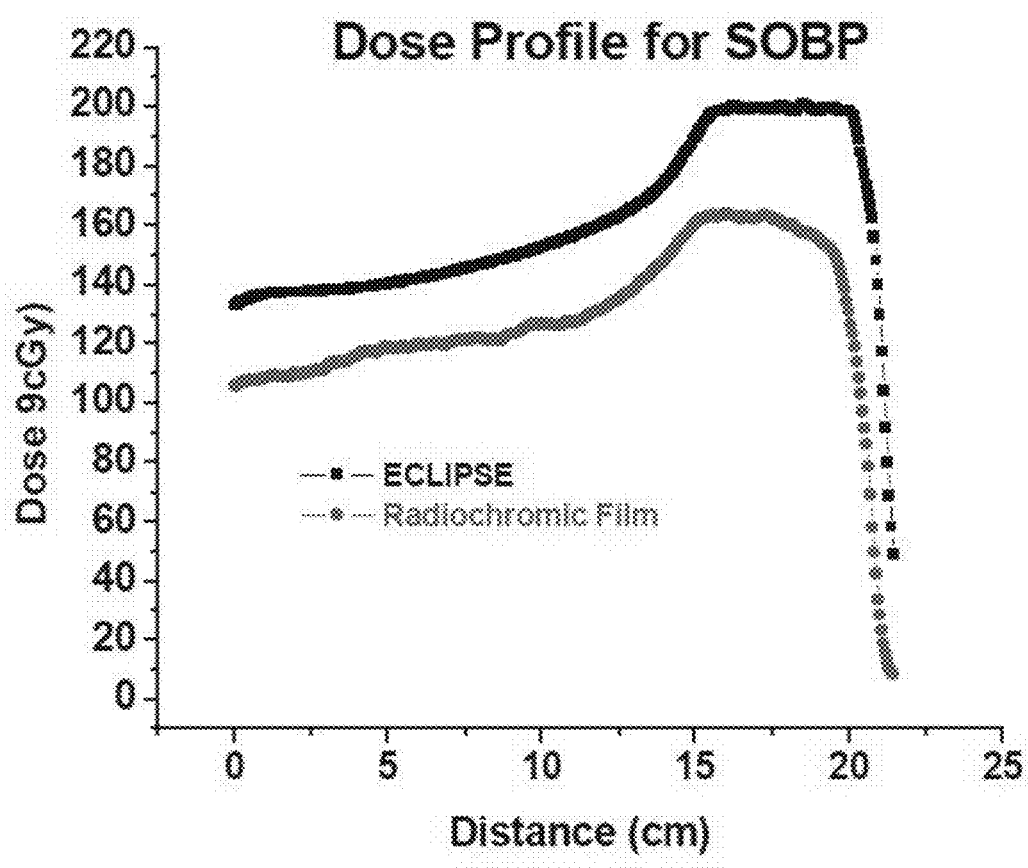
FIG. 11A is a graph of dose profiles of SOPB from ECLIPSE and Radiochromic film.
Figure 11B:
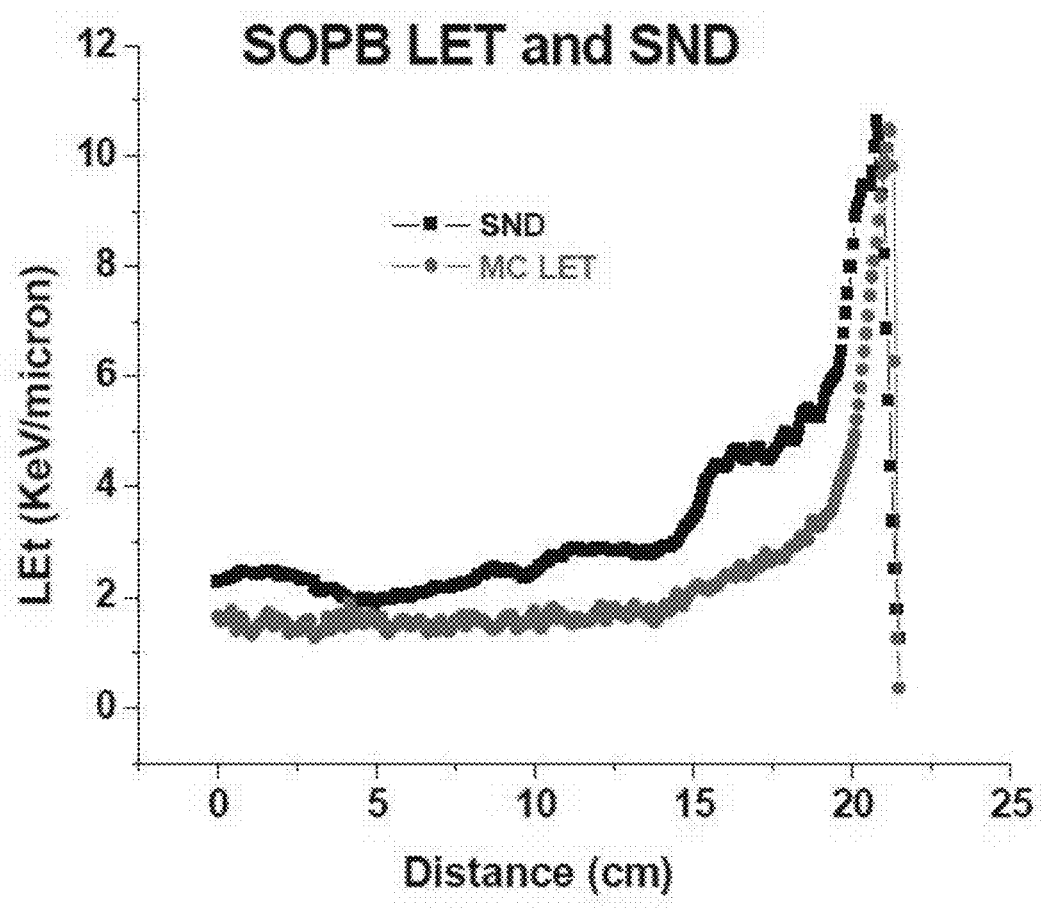
FIG. 11B is a graph of dose profiles of SND and LET for SOPB.
Figure 11C:
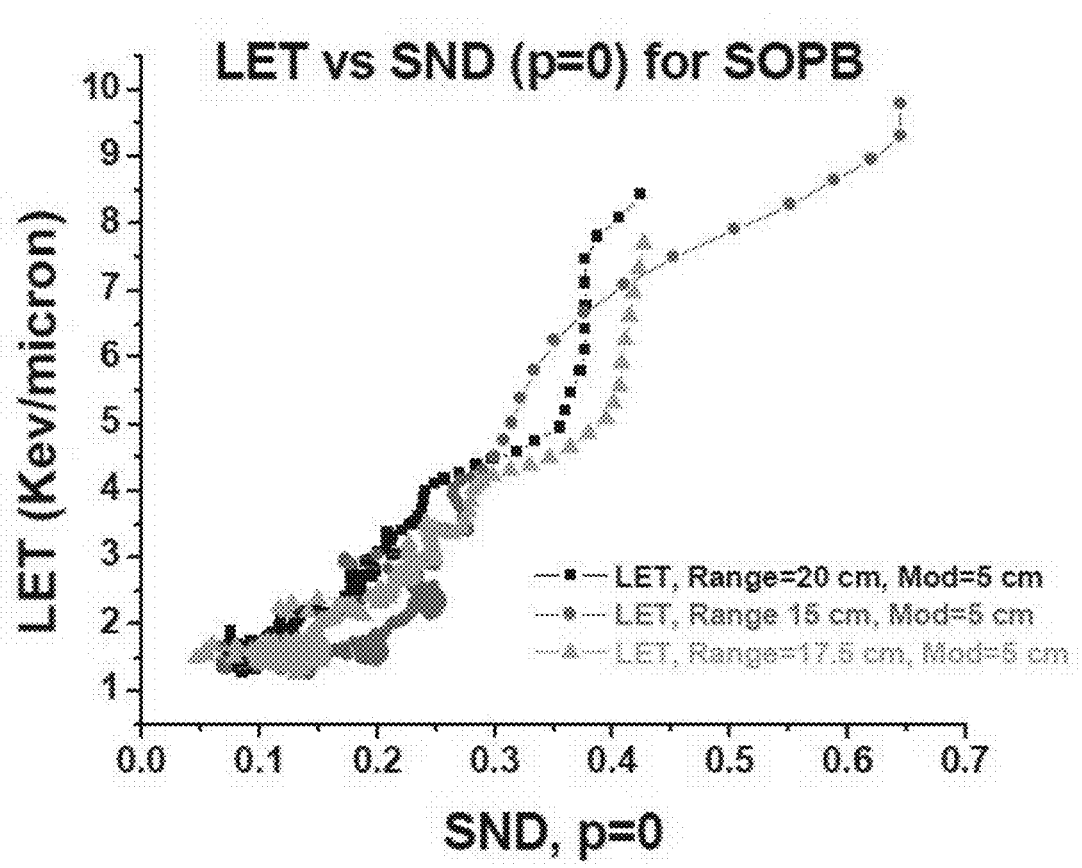
FIG. 11O is a graph of LET vs SND for SOPB for Ranges 15, 17.5, and 20 cm and modulation of 5 cm.
FIG. 11D is a graph of a LET profile for SOPB, proton range 20 cm, modulation 5 cm. and polynomial fits using 3, 4, 5 degrees and applied to SND with p=0.
Figure 11D:
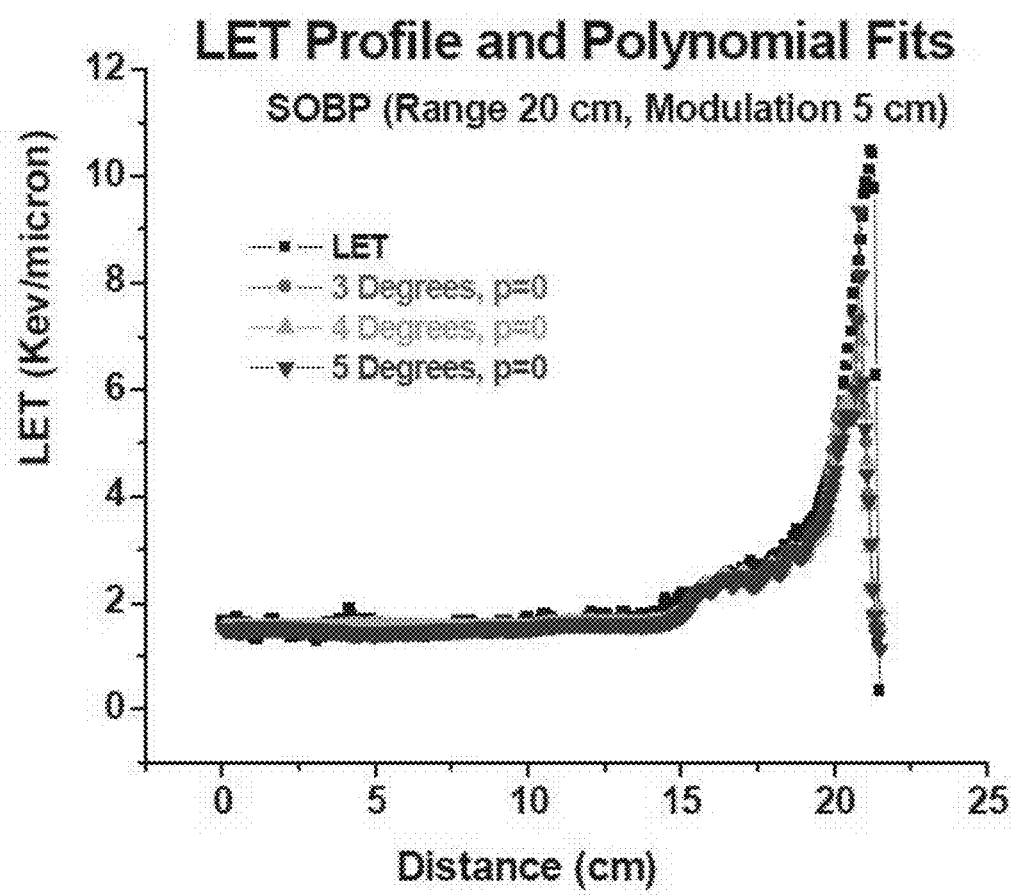

Profiles for the ECLIPSE and measured doses are shown in FIG. 11A. The SND and the LET profile for the broadened Bragg peak are shown in FIG. 11B. FIG. 11C shows that SND profile is correlated with the LET profile for the SOPB, albeit not as strongly as for the narrow Bragg peak for proton ranges of 15, 17.5, and 20 cm. The correlation coefficient R for the linear fit of LET to SND were 0.928, 0.948, and 0.963. However, there is greater overlap in the curves relative to the narrower Bragg peak (FIG. 6). The 3, 4, and 5 degree polynomial fits applied to the SND are shown in FIG. 11D.

Figure 12:
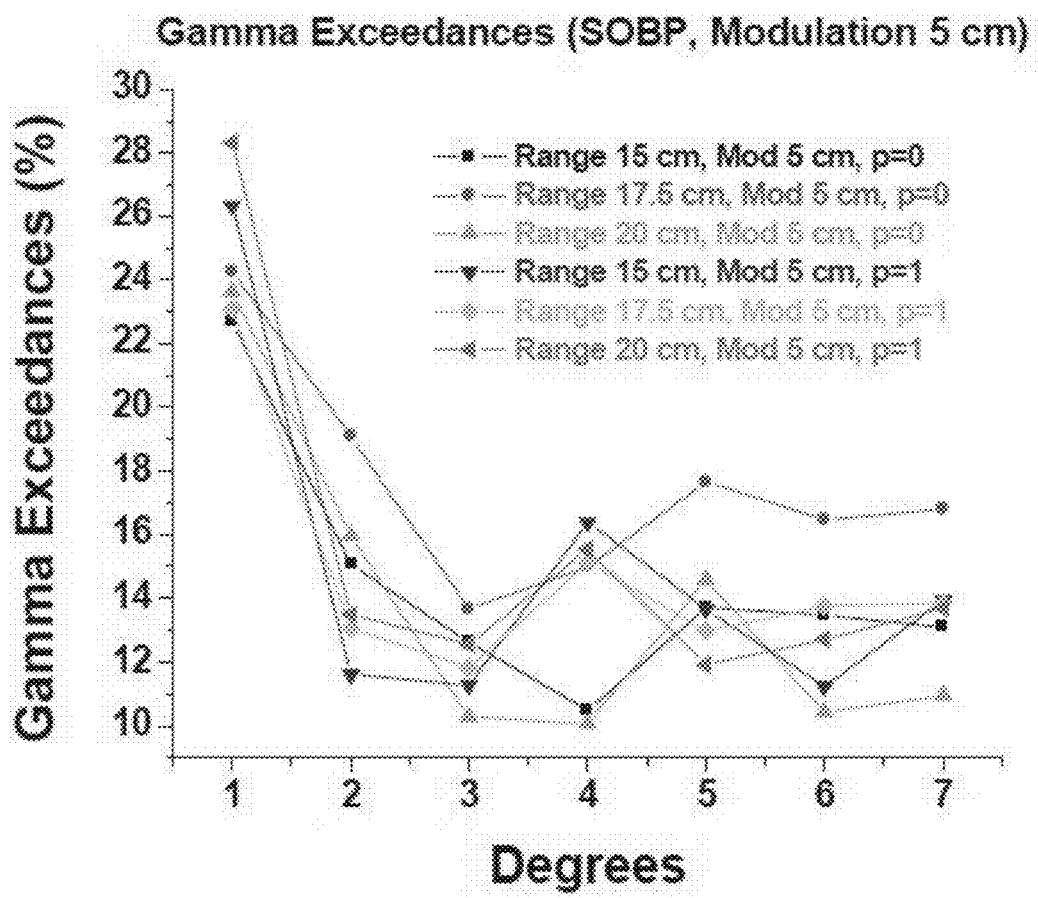
FIG. 12 a graph of gamma exceedances for SOPB (Modulation of 5 cm) proton ranges 15, 17.5, and 20 cm using polynomial corrections with degrees varying from 1 to 7 applied to SND (p=0, 1).

The gamma exceedances for the SOPB as a function of number of degrees in the polynomial fit are shown in FIG. 12 for protons having ranges of 15, 17.5, and 20 cm. FIG. 12 also shows the gamma exceedances that result from using exponents of p=0 and p=1 (Equation 7). For SOPB, the gamma exceedances are independent of the number of degrees in the polynomial fit for degrees >2. The higher number of degrees however can demonstrate high variability, especially for areas with high spatial gradients. The p=0 and p=1 exponent SND yields comparable number of gamma exceedances. The SOPB gamma exceedances are slightly larger than those from the narrower Bragg peaks. The statistical error in the number of exceedances is small due to the large number of pixels in the region of interest (roughly 10,000). The error in the measured exceedances is due to sensitivity to spatial registration, especially at the beam edges, and is roughly 1-2 percent.

DISCUSSION

The Applicants examined a number of metrics to relate the disparity in the absolute measured and treatment dose to the LET before opting for the SND (Equation 8). Specifically, the Applicants calculated and tested the ratio $R_1=(D_{TPS}/D_{RC})$, $R_2=1-1/R_1$, and $R_3=R_1*(D_{TPS}-D_{RC})$ to assess the LET. $R_1$, $R_2$, and $R_3$ qualitatively resemble the LET distribution Pixels with low $R_1$, $R_2$ were insensitive to LET (data not shown) and uncorrelated with LET. SND correlates better with the LET for all ranges of SND. Finding an appropriate mapping between SND and LET is simpler and more robust for proton LET corrections with ranges of 12.5, 15 cm. and SOPB with 15 cm and 17.5 cm. Although SND (Equation 8) is an admittedly crude measure for LET, it is empirically found to yield the best correlation with the MC LET over the largest dynamic range of SNDs.

The exact mechanism for quenching is uncertain. The consensus believes that quenching is attributed to localized saturation of monomer ionization due to the intense track density for high LET radiation. The Applicants developed a mathematical formulation (Equation 4) describing quenching and saturation and the relative sensitivity. The Applicants also found an empirical, heuristic approach (Equation 8) that invokes saturation and connects the reduced sensitivity of the radiochromic films for a proton beam with the increase of LET and limited polymerization. Alternatively, others ascribed the quenching to proton ionizing outside the sensitive layer.

Calculations can generate a number of different types of LET, specifically fluence and dose averaged LETs. Each LET also has lower bound cutoffs. Monte Carlo calculations generated the different LETs for this experimental situation.

The quantitative differences in the computed types of LET with the experimentally appropriate cut-offs were found to be small.

One way to describe dose saturation for radiochromic film is the invoked law of mass action. Similarly, modified law of mass action applied to LET can also help justify the approach used in this manuscript. The monomer fraction ($\mu$) and fraction of polymers ($\rho$) is conserved within the sensitive layer of the film:

$$\mu+\rho=1 \qquad (11)$$

Following mass action, the monomers serve as a source for the polymers if the monomers are ionized by radiation. The rate of polymerization depends on the local spatial ionization distribution or LET requires $\eta$ monomers:

$$\frac{d\rho}{d(LET)} = k\mu^\eta \qquad (12)$$

Where k is a constant. If $\eta=1$, then using Equation 11 and solving Equation 12, yields:

$$\rho=1-e^{-k(LET)} \qquad (13)$$

Equation (13) is identical to Equation (3) combined with Equation (6). Two different derivations yield the same saturating result.

Using multiple monomers to initiate polymerization, if $\eta>1$ then the polymerization fraction $\rho$ is:

$$\rho = 1 - \left(\frac{1}{kLET(\eta-1)}\right)^{1/(\eta-1)} \qquad (14)$$

For r>1 Equation 14 implies a minimum LET to initiate polymerization, where $LET_m$ in is:

$$LET_{min} = \frac{1}{k(\eta-1)} = \frac{E}{m(\eta-1)} \qquad (15)$$

by using Equation 6. Equation 14 and also be written as (using Equation 15):

$$\rho = 1 - \left(\frac{LET_{min}}{LET}\right)^{\frac{1}{\eta-1}} \qquad (16)$$

Applicants examined the possibility that the disparity between measured and calculated proton dose distribution could be attributed to experimental artifacts and not to LET. One possible artifact is the material difference between the radiochromic film and water or tissue equivalent material. The film manufacturer closely matched the film and phantom material. There is a slight difference in effective Z for the EBT2 and water (6.84 vs 7.42) and mass density (1.2-1.35 vs 1.0 gm/cc). Because photoelectric effect dominates the ionization cross section for the low energies, material differences suggest that the protons would have a longer range in the film if material differences explain the disparity. However, the film sensitivity is reduced (not increased) for all regions and all the measured and calculated ranges, even for higher energy protons where compositional differences between film and solid water should be most apparent. In addition, if compositional differences were significant, the off axis film dose distribution should exhibit curvature relative to calculated dose due to the longer proton path. Significant disparity in measured and calculated doses for off axis is, however, absent.

Directing the beam parallel to the film could possibly affect the measured results. In fact, others have found negligible angular dependence for this geometry unless air gaps exist between the film and phantom. The presence of air gaps manifests itself in increased detected measured dose. Instead, Applicants found lower measured dose relative to the calculated dose. Therefore, air gaps are absent and therefore no expected beam angular independence is expected.

Generating an LET spatial distribution map should have high degree of spatial registration between the treatment plan, the Monte Carlo LET calculation, and the measured dose distribution. The beam edges and distal edge of the Bragg peak showed enhanced number of gamma exceedances probably due to these registration issues.

Applicants' focused their examination on the unscatterred, high energy primary protons, rather than the scattered protons outside the main field. The scattered protons have very low energy but very high LET based on the Monte Carlo calculations (for example FIGS. 6A and 120). To experimentally probe these low dose regions, preferably there is greater signal to noise from the radiochromic film and therefore greater proton exposure times. These low dose regions may also require further examination of the SND and to possibly other exponents, beyond the p=0, 1 and other metrics.

This new tool can potentially measure and test LET in clinically significant configurations such as regions involving tissue heterogeneity. The radiochromic film, unlike the BANG gel may possibly be applied for measuring the LET in variable density regions by inserting the film between suitable phantom materials.

This modified film methodology provides an experimental areal LET measurement that can verify Monte Carlo measurements and support inferences from current LET point measurements. These LET measurements may enhance biologically based treatment planning for protons. For example, many large tumors have central hypoxic regions that are particularly radiation resistant. Directing the distal edge of the Bragg peak where the LET is high onto the hypoxic areas may elevate killing of these difficult to treat lesions. Depositing the distal edge of the Bragg peak to the hypoxic regions means adjusting the proton range and initial proton energy relative to more conventional treatments. Normally the entire target is treated using a spread out Bragg peak that requires beam modulation. If LET and biological response is incorporated into the treatment plan, a novel spread out LET distribution may be required. Glioblastoma is a particularly radio-resistant tumor and like hypoxic regions of the tumor benefit by accounting for the LET in the beam as well biological response. The transverse field edges will likely require only small adjustments.

More precise measurements may also help refine and determine the polymerization model and process. In particular, changing the dose levels may help discriminate between the multiple hit saturation model and the mass action models described herein. Within the mass action model, it is possible that 1, 2 or more monomers may be needed to promote the polymerization process and better measurements may determine the correct model.

Methods of Treatment and Treatment Planning

In some embodiments, a method of treating an abnormal condition using radiation therapy in a patient in need thereof, includes: subjecting the patient to a radiation source for at least one time point and measuring the Linear Energy Transfer (LET) deposited by a proton beam over one or more extended areas by analyzing a film dosimeter. An example of the film dosimeter is radiochromic or Gafchromic EBT2 film. As described above, the use of the radiochromic film can be used to measure the spatial distribution of the LET deposited by protons using a mathematical model correlating the film sensitivity and the LET. For example, the LET deposited over an area is extrapolated from dose derived from film measurements. The films are scanned and the recorded grey-levels are converted to dose with the help of calibration films. The experimental derived film dose is compared to dose calculation to generate the SND (described earlier). As previously noted, the SND is correlated with LET. The measured LET is compared to the calculated LET from Monte Carlo calculations to help verify treatment planning. In addition, the measured LET can then be converted to biological response. Such an enterprise may be beneficial for ensuring better therapy in heterogeneous areas such as for treating lung tumors and ensuring that tumors are eradicated while normal tissues are spared.

Once the spatial distribution of the LET is determined, one can determine a focused target area for the radiation treatment of the patient using the measured LET. The focused target area may include an abnormal growth, such as a malignant or benign tumor. As noted earlier, radiation resistant tissues such as hypoxic volumes within tumors may be particularly amenable to dose from the toxic high LET portions of the beam. The high LET portions reside in the distal edge of the Bragg peak and it is spatially narrow. Depositing the distal edge of the Bragg peak to the hypoxic regions means adjusting the proton range and initial proton energy relative to more conventional treatments. Normally the entire target is treated using a spread out Bragg peak that requires beam modulation. If LET and biological response is incorporated into the treatment plan, a developing and depositing a novel spread out LET distribution may be required. Glioblastoma is a particularly radio-resistant tumor, like hypoxic regions of the tumor, it may also benefit by accounting and exploiting the LET in the beam as well biological response to help eradicate the tumor. The transverse field edges will likely require only small adjustments. Patient immobilization requirements combined with in-situ patient imaging should be particularly stringent due to the spatially narrow LET regions. "Feathering" or combining beam edges from multiple proton beams is particularly difficult. Treatment should be bolstered by incorporating biological response to LET from the particle beams, and treatment planning could incorporate LET into their calculation to improve treatment.

Once the focused target area of the patient is determined, it can be dosed with a therapeutically effective amount of radiation while the dose of radiation to normal tissue surrounding the focused target area.

In some embodiments, the patient may be treated with a radiation source multiple times. In between treatments, the LET deposited by a proton beam may again be measured over an extended area to determine the spatial distribution of the LET deposited by protons so that a revised focused target area for the radiation treatment may be determined. The patient may be treated again by directing the proton beam to the revised focused target area with a therapeutically effective amount of radiation. The revised focused target area may be smaller than the original focused target area.

Apparatuses for Treating a Patient

Figure 13:
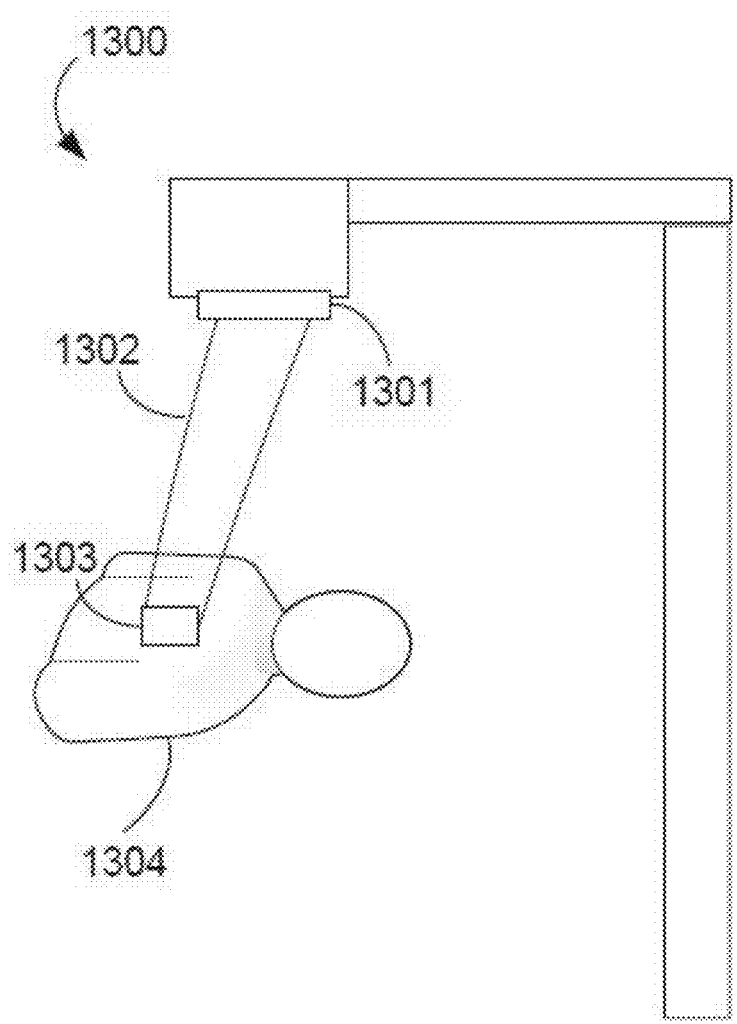
FIG. 13 is a diagram of an apparatus for treating a patient in accordance with some embodiments of the present invention.

Radiotherapy can be used to treat a patient with cancer by destroying cancer cells and slow tumor growth. One form of radiotherapy treatment is using an external beam of radiation made up of protons. FIG. 13 is a diagram of an apparatus for treating a patient in accordance with some embodiments of the present invention. The proton beam generator 1300 produces a proton beam 1302 for treating a patient 1304 using radiotherapy. The proton beam generator 1300 may be adjustable so as to vary the dose, proton range and/or the initial proton energy. The proton beam generator 1300 can be controlled by a software program using treatment planning software. The patient may have a tumor (not shown) within a treatment area 1303 of the patient. In order to direct and shape the proton beam to the treatment area 1303, the proton beam generator 1300 may include a beam shaper 1301, such as a collimator. The beam shaper may be configured based on a previously measured Linear Energy Transfer (LET) deposited by a proton beam over an extended area using radiochromic film describe above. This can allow for the treatment area 1303 to be better focused then determination using conventional means. The control of the beam shaper can be by a software program using treatment planning software.

Although the present invention has been described in connection with embodiments thereof, it will be appreciated by those skilled in the art that additions, deletions, modifications, and substitutions not specifically described may be made without departure from the spirit and scope of the invention as defined in the appended claims.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically "adapted/adaptable," "able to," "conformable/conformed to," etc. Those skilled in the art will recognize that such terms (e.g., "configured to") can generally encompass active state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically interacting, and/or logically interactable components.

In some instances, one or more components may be referred to herein as "configured to," "configured by," "configurable to, "operable/operative to," means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A method of treating an abnormal condition using radiation therapy in a patient in need thereof, the method comprising: subjecting the patient to a radiation source for at least one time point and measuring the Linear Energy Transfer (LET) deposited by a proton or ion beam over one or more extended areas by following the analysis of a film dosimeter; and determining a focused target area for the radiation treatment of the patient using the measured LET over at least one of the one or more extended areas, and dosing the focused target area of the patient with a therapeutically effective amount of radiation.

2. The method of claim 1, wherein analyzing the film dosimeter includes: scanning the film to record grey-levels of the film; converting the grey-levels to a measured dose using calibration films; and comparing the measured dose to a calculated dose to generate scaled normalized difference (SND) between the calculated dose and the measured dose.

3. The method of claim 1, further comprising adjusting a proton or ion range and initial proton or ion energy of the proton or ion beam based on the measured LET.

4. The method of claim 3, wherein the proton or ion range and the initial proton or ion energy are adjusted such that hypoxic volumes within the focused target area are dosed by toxic high LET portions of the proton or ion beam.

5. The method of claim 1, wherein the film dosimeter is radiochromic film.

6. The method of claim 1, wherein the focused target area is an abnormal growth.

7. The method of claim 6, wherein the abnormal growth is a malignant or benign tumor.

8. The method of claim 1, wherein the focused target area includes regions involving tissue heterogeneity.

9. The method of claim 1, wherein the treatment reduces the dose of radiation to normal tissue surrounding the focused target area.

10. The method of claim 1, further comprising: subjecting the patient to the radiation source for at least one additional time point after dosing the focused target area with radiation at least one time and measuring the LET deposited by a proton or ion beam over one or more extended areas using a film dosimeter; determining a revised focused target area for the radiation treatment of the patient using the measured LET over at least one of the one or more extended areas; and dosing the revised focused target area of the patient with a therapeutically effective amount of radiation.

11. The method of claim 10, wherein the revised focused target area is smaller than the first focused target area.

12. An apparatus for treating a patient, comprising: a proton or ion beam generator configured to provide a proton or ion beam to a patient; control of the proton or ion energy in order to control the depth of the particles inside the treated volume; and a beam shaper to shape the proton or ion beam to a focused target area of the patient, wherein the beam shaper is capable of being configured based on a previously measured Linear Energy Transfer (LET) deposited by a proton or ion beam over an extended area.

13. The apparatus of claim 12, wherein the previously measured LET is measured using radiochromic film.

14. The apparatus of claim 12, wherein the beam shaper is a collimator control of the proton transverse spatial distribution and proton or ion energy in order to control the depth of the particles inside the treated volume.

15. The apparatus of claim 12, wherein the beam shaper is controlled by a software program based on a prescribed treatment plan.

16. The apparatus of claim 12, wherein the proton beam generator is capable of adjusting the proton or ion range and initial proton energy of the proton beam based on the previously measured LET.

17. A method of measuring Linear Energy Transfer (LET) deposited over an area, comprising: dosing a film with a proton or ion beam; scanning the film to record greylevels of the film from red, green, blue channels of a color scanner); converting the grey-levels to a measured dose using calibration films; and comparing the measured dose to a calculated dose to generate scaled normalized difference (SND) between the calculated dose and the measured dose.

18. The method of claim 17, wherein the calculated dose is determined using a Treatment Planning System (TPS).

19. The method of claim 17, further comprising: correlating the SND to a measured LET; and comparing the measured LET to a calculated LET from Monte Carlo calculations to verify treatment planning.

20. The method of claim 17, wherein the film is radiochromic film.

* * * * *